United States Patent [19]

Servais

[11] Patent Number: 4,861,926
[45] Date of Patent: Aug. 29, 1989

[54] STABILIZED 1,1,1-TRICHLOROETHANE COMPOSITIONS

[75] Inventor: Michel Servais, Kraainem, Belgium

[73] Assignee: SOLVAY & Cie (Societe Anonyme), Brussels, Belgium

[21] Appl. No.: 615,511

[22] Filed: May 31, 1984

Related U.S. Application Data

[63] Continuation-in-part of Ser. No. 586,871, Mar. 6, 1984, which is a continuation of Ser. No. 367,909, Apr. 13, 1982, abandoned.

[30] Foreign Application Priority Data

Apr. 13, 1981 [FR] France ............................. 81 07528
Jun. 9, 1983 [FR] France ............................. 83 09718

[51] Int. Cl.4 ..................... C07C 17/42; C07C 19/05
[52] U.S. Cl. ..................................... 570/110; 570/104
[58] Field of Search ................ 570/104, 110, 114, 116

[56] References Cited

U.S. PATENT DOCUMENTS

| | | | |
|---|---|---|---|
| 3,060,125 | 10/1962 | Sims ..................................... | 570/110 |
| 3,848,004 | 11/1974 | Katsuragawa et al. ............. | 570/110 |
| 3,957,893 | 5/1976 | Beckers et al. ...................... | 570/110 |
| 4,351,973 | 9/1982 | Ishibe et al. .......................... | 570/104 |

FOREIGN PATENT DOCUMENTS

| | | |
|---|---|---|
| 858017 | 2/1978 | Belgium . |
| 62952 | 10/1982 | European Pat. Off. . |
| 2119749 | 8/1972 | France . |
| 2503697 | 10/1982 | France . |

*Primary Examiner*—J. E. Evans
*Attorney, Agent, or Firm*—Spencer & Frank

[57] ABSTRACT

Stabilized 1,1,1-trichloroethane compositions containing an epoxide compound such as epoxybutane, a nitro compound such as nitromethane, a furan compound such as 2-methylfuran, and methyl acetate. These compositions are suitable for the degreasing of metals and for the dry cleaning of textiles in the presence of an aqueous phase.

5 Claims, No Drawings

STABILIZED 1,1,1-TRICHLOROETHANE COMPOSITIONS

CROSS-REFERENCE TO RELATED APPLICATIONS

This application is a continuation-in-part of U.S. Ser. No. 06/586/871, filed Mar. 6, 1984, which is a continuation of U.S. Ser. No. 06/367,909 filed Apr. 13, 1982, now abandoned.

BACKGROUND OF THE INVENTION

1. Field of the Invention

The present invention relates to stabilized 1,1,1-trichloroethane compositions which can be used, in particular, for the degreasing of metals and for the dry cleaning of textiles.

2. Description of the Related Art

It is known that 1,1,1-trichloroethane, which is used, in particular, for the degreasing of metals, for the dry cleaning of textiles and in aerosols, presents a very particular problem of stability and corrosion. Satisfactory results are not generally obtained if the stabilizers normally used for other chlorohydrocarbons are used the stabilizing 1,1,1-trichloroethane. This phenomenon has been attributed especially to the fact that there is a high degree of reactivity between 1,1,1-trichloroethane, metals such as aluminium, zinc and their alloys, and water. Consequently, a large number of various stabilized compositions have been developed which are specific for 1,1,1-trichloroethane. Among these compositions, there may be mentioned, in particular, ternary compositions based on epoxides, nitroalkanes and dioxane, described in U.S. Pat. No. 3,049,571 filed on Mar. 18, 1960 by THE DOW CHEMICAL CO. However, none of the compositions proposed hitherto is really effective. In particular, no known composition of 1,1,1-trichloroethane has a satisfactory stability under extremely harsh conditions such as those prevailing when light metals and water are present simultaneously.

To solve this problem, the Applicant Company has already proposed, in European Patent Application No. 82200418.0 of Apr. 2, 1982, now EP-A1-0 062 952, which corresponds to U.S. Ser. No. 06/586,971 filed Mar. 6, 1984, which is a continuation of U.S. Ser. No. 06/367,909 filed Apr. 13, 1981, of which the present application is a continuation-in-part, stabilized 1,1,1-trichloroethane compositions containing an epoxide compound, a nitro derivative and an internal ether of the furan type. Although these compositions give excellent results under the harsh conditions of use, when the quantity of water is greater than the water saturation level of the organic phase, they present a difficulty in the separation of the organic and aqueous phases. Thus, it is found that complete separation by settling of the aqueous phase is excessively slow.

SUMMARY OF THE INVENTION

The aim of the present invention is to overcome this disadvantage of the known compositions and to provide stabilized 1,1,1-trichloroethane compositions permitting perfect and virtually instantaneous settling of the aqueous phase.

For this purpose, the invention relates to stabilized 1,1,1-trichloroethane compositions containing an epoxide compound, a nitro compound, a furan compound and an alkyl ester, in which the alkyl ester is methyl acetate.

The term "epoxide compound" is understood as meaning saturated or unsaturated aliphatic compounds containing at least one epoxide group in their molecule. Preferably, the compositions according to the invention contain saturated aliphatic compounds containing from 3 to 6 carbon atoms in their molecule, such as epoxypropane, epoxybutane, 2-methylepoxypropane, 2-methylepoxybutanes, glycidol and epichlorohydrin. Good results have been obtained with 2-methyl-2,3-epoxybutane and epoxybutane.

The total quantity of epoxide compound present in the compositions according to the invention usually varies between 0.01 and 50 grams per liter. Preferably, this quantity is between 0.1 and 20 grams per liter. Quantities of between 1 and 10 grams per liter are very particularly preferred.

The nitro compounds present in the compositions according to the invention are preferably nitroalkanes containing from 1 to 4 carbon atoms in their molecule. Good results have been obtained with nitromethane, nitroethane and 1-nitropropane or 2-nitropropane. Nitroethane and, especially, nitromethane are very particularly preferred.

The quantities of nitro compounds are the same as those defined for the epoxide compounds.

The term "furan compound" is understood as denoting furan and also furan derivatives in which some hydrogen atoms are substituted by other elements or groups and more particularly by saturated aliphatic groups containing from 1 to 5 carbon atoms.

Generally, in the substituted derivatives of furan, the furan nucleus is substituted by only one or two aliphatic groups and the substitution positions are usually on the 2 and 5 carbon atoms of the furan nucleus.

The preferred furan compounds include 2-methylfuran, 2-ethylfuran, 2-isopropylfuran, 2-propylfuran and 2,5-dimethylfuran. The best results have been obtained with 2-methylfuran, which is very particularly preferred.

The quantities of furan compound present in the compositions according to the invention generally vary between 0.1 and 100 grams per liter. Preferably, this quantity is between 1 and 75 grams per liter. Quantities of between 5 and 50 gramns per liter are very particularly preferred.

The quantity of methyl acetate present in the compositions according to the invention generally varies between 0.01 gram and 50 grams per liter. This quantity is preferably between 0.1 and 20 grams per liter. Quantities of between 0.2 and 10 grams per liter are very particularly preferred.

The compositions according to the invention can be used in any applications requiring a good stability of the 1,1,1-trichloroethane. They can be used under harsh conditions and, in particular, in the simultaneous presence of metallic elements, especially the light metals, and water.

Thus, the compositions according to the invention are particularly suitable when the process is carried out in the presence of a quantity of water greater than the water saturation level of the organic phase, that is to say when the process is carried out in contact with an aqueous phase, requiring perfect setting of the organic phase and the aqueous phase.

The compositions of the invention also have an excellent suitability for recycling.

DESCRIPTION OF THE PREFERRED EMBODIMENTS

The example which follows, which in no way implies a limitation, shows the improved settling of the organic phase and the aqueous phase which is observed with the compositions according to the invention (Experiment 1) by comparison with another composition of the same type (Experiment 2), not containing methyl acetate.

EXPERIMENT 1

500 cm$^3$ of 1,1,1-Trichloroethane, stabilized by means of 4 g/liter of 1,2-epoxybutane, 5 g/liter of nitromethane, 30 g/liter of 2-methylfuran and 2 g/liter of methyl acetate, are introduced into a 1000 cm$^3$ round-bottomed flask equipped with a condenser and connected to a source of steam.

Steam at 110° C. is then introduced into the bottom of the flask and the mixture is distilled by steam distillation until 99.3% of the quantity of 1,1,1-trichloroethane used has been recovered.

The distillate is left to settle and 100 cm$^3$ of stabilized 1,1,1-trichloroethane are recovered in a cylinder.

An aqueous phase which has settled well out of the organic phase and is very clear is obtained instantaneously.

EXPERIMENT 2

The procedure of Experiment 1 is followed, but the 1,1,1-trichloroethane used is stabilized by means of 4 g/liter of epoxybutane, 5 g/liter of nitromethane and 30 g/liter of 2-methylfuran.

As in Experiment 1, an aqueous phase which has settled well out of the organic phase is obtained, but an hour is necessary for the aqueous phase to become clear.

What is claimed is:

1. Stabilized 1,1,1-trichloroethane composition for use in the presence of water in an amount of water in excess of the saturation level of the stabilized composition, said composition comprising:
   1,1,1-trichloroethane;
   an epoxide compound;
   a nitro compound;
   a furan compound; and
   methyl acetate,
   wherein said composition is stable in the presence of water and metals, and
   wherein said composition immediately separates into a separate non-aqueous phase after being mixed with water in an amount greater than the saturation level of said composition.

2. The composition according to claim 1, wherein the methyl acetate is present in quantities of between 0.1 and 20 grams per liter.

3. The composition according to claim 1, wherein the furan compound is selected from the group consisting of 2-methylfuran, 2-ethylfuran, 2-isopropylfuran, 2-propylfuran and 2,5-dimethylfuran.

4. The composition according to claim 3, wherein the furan compound is 2-methylfuran.

5. The composition according to claim 2, wherein the furan compound is selected from the group consisting of 2-methylfuran, 2-ethylfuran, 2-isopropylfuran, 2-propylfuran and 2,5-dimethylfuran.

* * * * *